United States Patent [19]

Dorontic

[11] Patent Number: 6,013,661

[45] Date of Patent: Jan. 11, 2000

[54] PROTECTION OF CROPS AGAINST BIRDS USING A COMPOUND OF PHENYLPYRAZOLE TYPE

[75] Inventor: Sinisa Dorontic, Zagreb, Croatia

[73] Assignee: Rhone-Poulenc Agrochimie, Lyons, France

[21] Appl. No.: 08/945,183

[22] PCT Filed: Apr. 18, 1996

[86] PCT No.: PCT/EP96/01625

§ 371 Date: Jan. 21, 1998

§ 102(e) Date: Jan. 21, 1998

[87] PCT Pub. No.: WO96/32842

PCT Pub. Date: Oct. 24, 1996

[30] Foreign Application Priority Data

Apr. 19, 1995 [FR] France .................................. 95/04940

[51] Int. Cl.[7] .......................... A01N 43/56; A01N 43/40; A01N 25/00
[52] U.S. Cl. .......................... 514/407; 514/341; 514/918; 424/405
[58] Field of Search .......................... 514/272, 403–407, 514/918, 341, 333; 424/405, 409, 410

[56] References Cited

U.S. PATENT DOCUMENTS

| 4,804,675 | 2/1989 | Jensen-Korte et al. .................. 514/407 |
| 5,232,940 | 8/1993 | Hatton et al. ........................... 514/407 |
| 5,306,694 | 4/1994 | Phillips et al. ........................... 504/253 |
| 5,364,626 | 11/1994 | Hasegawa et al. ..................... 424/403 |
| 5,451,598 | 9/1995 | Salmon .................................. 514/404 |
| 5,716,977 | 2/1998 | Colliot et al. ........................... 514/407 |

FOREIGN PATENT DOCUMENTS

| 0295117 | 12/1988 | European Pat. Off. . |
| 0500209 | 8/1992 | European Pat. Off. . |
| 87/03781 | 7/1987 | WIPO . |
| 93/06089 | 4/1993 | WIPO . |
| 94/21606 | 9/1994 | WIPO . |

*Primary Examiner*—John Pak
*Assistant Examiner*—Frank Choi
*Attorney, Agent, or Firm*—Burns, Doane, Swecker & Mathis, L.L.P.

[57] ABSTRACT

Process for the protection of crops against birds, characterized in that an effective amount of 1-phenylpyrazole compound is applied to the said crop or to the cultivated region comprising the said crop or to the seed.

29 Claims, No Drawings

PROTECTION OF CROPS AGAINST BIRDS USING A COMPOUND OF PHENYLPYRAZOLE TYPE

This application is a 371 of PCT/EP96/01625, filed Apr. 18, 1996.

The present invention relates to a new process for repelling birds and to a new process for protecting crops against birds.

Each year during winter, birds cause considerable damage to cereal sowings by attaching either the grain itself, which, being still only lightly buried, can easily be unearthed by birds, or the young plantlet, as soon as the latter emerges from the ground. The birds which cause damage are in particular the Corvidae (crows and others), the Sturnidae (starlings and others), the passerines, the Galliformes (in particular pheasants and partridges) and the Columbiformes (in particular pigeons and turtledoves).

The effect of this damage on the future harvest is reflected by very large falls in yield.

For a long time, farmers have only had available means of their own devising for controlling birds (scarecrow, firecrackers and the like).

The protection of crops against birds remains a permanent problem. Legislation for protecting the environment is becoming increasingly strict and, in particular, it increasingly protects birds, harmful or otherwise. Designating certain species as harmful animals makes it permissible to destroy them, under less draconian regulations, but it is increasingly difficult legally to designate birds as harmful animals which are in reality and in practice harmful.

It is therefore desirable to have available bird-repellent agents. It is also desirable to have available new bird-repellent agents in order for the birds not to become used to the repellent agents and not to become insensitive to their presence.

The prediction of the repellent nature of such and such a product is all the more difficult since some products are attractive for some categories of animals and repellent for others, without there being a general rule to guide the choice in one direction or the other.

It is also desirable to have available bird-repellent agents which have a good persistence of action. Indeed, birds attack grains throughout the period ranging from sowing until the time when the young plantlet emerging from the seed reaches a certain stage of development.

At this point, the seed of a cereal is devoid of its nutrient substance and is therefore no longer capable of being of interest to a bird in search of food. A good repellent must therefore exert its effect for a period sufficient to enable the cereal to reach this stage of development.

It is also desirable to have available a repellent which has a low toxicity for game which has to be protected, it being possible for this toxicity to be low either in itself or as a result of the small size of the doses applied.

An object of the present invention is to provide a new process for the protection of crops against birds.

Another object of the present invention is to provide a process for the protection of crops against birds which has none or few of the disadvantages of known repellents and which corresponds, in all or part, to the quality objectives required for an ideal repellent.

Another object of the present invention is to provide a process for the protection of crops against harmful birds and against harmful insects simultaneously.

Another object of the present invention is to provide a new process for repelling birds.

Another object of the present invention is to provide new compositions which are repellent with respect to birds.

It has now been found that these aims could be achieved by virtue of compositions comprising, as bird-repellent active material, 1-phenylpyrazoles and preferably 1-phenylpyrazoles of general formula (I).

The 1-phenylpyrazoles capable of being employed in the invention are therefore advantageously products of formula (I):

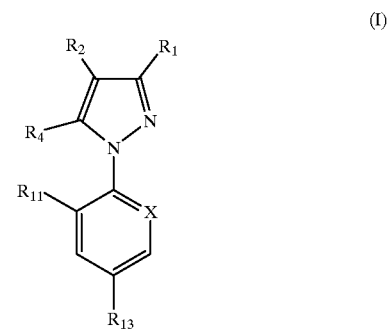

in which:
$R_1$ is CN or methyl;
$R_2$ is $S(O)_n R_3$;
$R_3$ is alkyl or haloalkyl;
$R_4$ represents a hydrogen or halogen atom or an $NR_5R_6$, $S(O)_m R_7$, $C(O)R_7$ or $C(O)O-R_7$, alkyl, haloalkyl or $OR_8$ radical or an $—N=C(R_9)$ $(R_{10})$ radical;
$R_5$ and $R_6$ independently represent the hydrogen atom or an alkyl, haloalkyl, C(O)alkyl, alkoxycarbonyl or $S(O)_r CF_3$ radical; or $R_5$ and $R_6$ can together form a divalent alkylene radical which can be interrupted by one or two divalent heteroatoms, such as oxygen or sulphur;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group which is optionally substituted by one or a number of halogen atoms or groups such as OH, -O-alkyl, -S-alkyl, cyano or alkyl;
$R_{11}$ and $R_{12}$ represent, independently of one another, a hydrogen or halogen atom;
$R_{13}$ represents a halogen atom or a haloalkyl, haloalkoxy, $S(O)_q CF_3$ or $SF_5$ group;
m, n, q, and r represent, independently of one another, an integer equal to 0, 1 or 2;
X represents a trivalent nitrogen atom or a C-$R_{12}$ radical, the other three valencies of the carbon atom forming part of the aromatic ring;
provided that, when $R_1$ is methyl, then $R_3$ is haloalkyl, $R_4$ is $NH_2$, $R_{11}$ is Cl, $R_{13}$ is $CF_3$ and X is N.

The compound of formula (I) employed in the invention can be a compound of the formula (II):

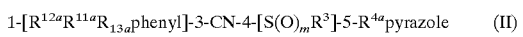

1-[$R^{12a}R^{11a}R_{13a}$phenyl]-3-CN-4-[S(O)$_m R^3$]-5-$R^{4a}$pyrazole  (II)

in which $R^{11a}$ and $R^{12a}$ represent a hydrogen or halogen atom in the 2 or 6 position on the phenyl ring, at least one of them being other than the hydrogen atom, $R_{13a}$ represents a halogen atom or a haloalkyl or haloalkoxy or $SF_5$ group in the position on the phenyl ring, $R^3$ represents an alkyl or haloalkyl group, $R^{4a}$ represents an amino group which is optionally mono- or disubstituted by an alkyl, haloalkyl, acyl or alkoxy group, n is 0, 1 or 2.

The alkyl groups in formulas (I) and (II) are preferably lower alkyl radicals.

A preferred class of compounds of formula (I) is composed of the compounds such that $R_1$ is CN, and/or $R_3$ is haloalkyl, and/or $R_4$ is $NH_2$, and/or $R_{11}$ and $R_{12}$ are, independently of one another, a halogen atom, and $R_{13}$ is haloalkyl.

A compound of formula (I) which is very particularly preferred in the invention is

1-[2,6-$Cl_2$-4-$CF_3$phenyl]-3-CN-4-[SO-$CF_3$]-5-$NH_2$pyrazole, hereinafter known as compound A.

The 1-arylpyrazoles of the present invention are effective for repelling with respect to birds of various natures such as those mentioned above.

Compounds of formula (I) can be prepared according to one or other of the processes described in Patent Applications WO 87/3781, 93/6089 or 94/21606 or European Patent Application 295,117, or any other process coming within the competence of the person skilled in the art who is a specialist in chemical synthesis.

Formulations which can be used in the invention are described in particular in these same Patent Applications. The formulations described in the prior art were prepared for an insecticidal purpose. The formulations or compositions for repelling birds may be similar or may be adapted in order to make them still more suitable for their repellent use, in particular by additions of appropriate adjuvants.

The formulations which are suitable for the employment of the process according to the invention contain from 0.0001 to 95% by weight of active material of formula (I). As regards the concentrated formulations for commercial use (for storage, sale or transportation), they advantageously contain from 0.1 to 15% by weight of active material. The compositions as used by the applicator are generally much more dilute compositions. In addition to this active material, the compositions according to the invention contain various solid or liquid vehicles, surfactants and other adjuvants of the most varied natures but which are environmentally acceptable.

The 1-arylpyrazoles employed in the invention can advantageously be formulated as fluid or liquid compositions, wettable powders or microemulsions. Such formulations generally comprise one or a number of solid or liquid inert vehicles or diluents which are agronomically acceptable.

Wettable powder or concentrated granule formulations can be prepared by milling a 1-arylpyrazole of formula (I) with approximately 1% to 20% by weight of solid anionic surfactant. A suitable anionic surfactant is the dioctyl ester of the sodium salt of sulfosuccinic acid. Approximately 85% to 95% by weight of inert diluent, such as montmorillonite, attapulgite, limestone, talc, kaolin, diatomaceous earth, pumice, silicates or other similar products, can be included in such formulations, as well as the other adjuvants indicated above.

In addition to the granules and wettable powders described above, use can be made of fluid formulations and in particular of formulations which are easily dispersable in water, in order to facilitate dispersion over the place of application, in particular in agriculture.

The pyrazoles which are used in the present invention have a low solubility but can be used at low doses. They can therefore be employed in solutions or emulsions or, preferably, in the form of aqueous or non-aqueous suspensions comprising the appropriate adjuvants and/or cosolvents. Acetone and methyl ether ketone can be used as cosolvents. Any liquid medium can be used, provided that it is neither toxic for plants nor for the environment. When the active material has little solubility, cosolvents and/or wetting or dispersing agents can be used. Other additives can also be employed, such as talc. Active materials of formula (I) can be absorbed onto vehicles, for example vermiculite, clay, talc, kaolin or others, in particular to form granules.

The 1-arylpyrazoles are also effective in protecting seeds, as well as plantlets or young seedlings or plants which are more advanced in maturity. The most varied crops can thus be protected, in particular wheat, maize, rice, barley, rye, beets and any plant which is sown or which passes through the plantlet stage.

The application of the 1-arylpyrazoles according to the invention is often carried out in the form of granules over the plants or over the soil of the crop which has to be protected. These applications in the form of granules are generally carried out so as to provide a dose of active material of approximately 0.01 kg/ha to approximately 1 kg/ha of active material and preferably between 0.02 and 0.3 kg/ha.

The 1-arylpyrazoles of the invention are also effective in protecting crops by application of the active material to the seed before sowing. The seed can be treated by coating or film coating or impregnation or immersion in a liquid or a pasty formulation known per se, followed by drying. A seed treatment so that the seed contains 2 to 1000 g per quintal of seed, preferably 5 to 800 g/q, is particularly appropriate.

The invention thus further comprises a process for the protection of crops against birds, characterized in that an effective amount of compound of general formula (I) is applied to the said crop or to the cultivated region comprising the said crop. This application to the crop can be carried out by application of a composition comprising the active material to the cultivated ground before sowing or after sowing. According to an advantageous alternative form of the invention, the invention is employed by application of an effective amount of compound of formula (I) to the seed which has to be sown.

The invention thus further relates to the use of compounds of formula (I) as repellents with respect to birds.

The invention thus further relates to seeds intended to be sown in a region frequented or capable of being frequented by birds, characterized in that they are treated with an active material or a composition as defined above.

The invention thus further relates to compositions intended to be distributed over a region frequented or capable of being frequented by birds, characterized in that they comprise an active material as defined above.

The following examples, given without implied limitation, illustrate the invention and show how it can be employed.

EXAMPLE 1

Maize seeds treated with an aqueous suspension of compound A so as to leave on the seeds an amount of active material of 625 g/quintal, which corresponds to 218 g/ha (35 kg of seeds per hectare).

The sowing is carried out in a field frequented by pheasants. The amount of seed remaining in the field after 3 days is measured and the result observed is expressed in the form of a percentage by number with respect to the amount of seed sown. 72% of the seed remains, instead of 23% for untreated controls.

EXAMPLE 2

The procedure is the same as in Example 1, but with sunflower seeds. 96% of the seeds remain, instead of 36% for the untreated control.

EXAMPLE 3

The procedure is the same as in Example 2, but with a field frequented by crows. 99% of the seeds remain, instead of 45% for the untreated control.

EXAMPLE 4

The procedure is the same as in Example 1, but with a field frequented by crows. 96% of the seeds remain, instead of 19% for the untreated control.

I claim:

1. A process for protecting crops said process comprising applying to crops, the cultivated region in which they grow, before or after sowing, or their seed, which are in need of protection from birds, in an amount effective to repel birds, a compound having the formula:

(I)

wherein:
  $R_1$ is CN or methyl;
  $R_2$ is $S(O)_n R_3$;
  $R_3$ is alkyl or haloalkyl;
  $R_4$ is hydrogen, halogen, $NR_5 R_6$, $S(O)_m R_7$, $C(O)R_7$, $C(O)O-R_7$, alkyl, haloalkyl, $OR_8$ or $-N=C(R_9)(R_{10})$;
  each of $R_5$ and $R_6$ is, independently, hydrogen, alkyl, haloalkyl, C(O)alkyl, alkoxycarbonyl or $S(O)_r CF_3$; or $R_5$ and $R_6$ together form a divalent alkylene radical which is interrupted by one or two divalent heteroatoms selected from the group consisting of oxygen and sulfur;
  $R_7$ is alkyl or haloalkyl;
  $R_8$ is alkyl, haloalkyl or hydrogen;
  $R_9$ is alkyl or hydrogen;
  $R_{10}$ is phenyl or heteroaryl which is unsubstituted or substituted by one or more halogen, OH, -O-alkyl, -S-alkyl, cyano or alkyl;
  X is a trivalent nitrogen atom or a $C-R_{12}$ radical, the other three valencies of the carbon atom forming part of the aromatic ring;
  each of $R_{11}$ and $R_{12}$ is, independently, hydrogen or halogen;
  $R_{13}$ is halogen, haloalkyl, haloalkoxy, $S(O)_q CF_3$ or $SF_5$; and
  each of m, n, q, and r is, independently, an integer equal to 0, 1 or 2;
  provided that, when $R_1$ is methyl, then $R_3$ is haloalkyl, $R_4$ is $NH_2$, $R_{11}$ is Cl, $R_{13}$ is $CF_3$ and X is N;
  wherein at least 72% of said crop, cultivated region or seed, which are in need of protection from birds, are effectively protected by the bird repelling action of said compound.

2. A process according to claim 1, wherein the compound of formula (I) has the formula:

(II)

wherein:
  each of $R_{11a}$ and $R_{12a}$ is hydrogen or halogen, at least one of them being other than hydrogen;
  $R_{13a}$ is halogen, haloalkyl, haloalkoxy or $SF_5$;
  $R_3$ is alkyl or haloalkyl;
  $R_{4a}$ is amino which is unsubstituted or is mono- or disubstituted by alkyl, haloalkyl, C(O)alkyl or alkoxycarbonyl; and
  n is 0, 1 or 2.

3. A process according to claim 1, wherein the compound of formula (I) is 5-amino-3-cyano-1-(2,6-dichloro-4-trifluoromethylphenyl)-4-trifluoromethylsulfinylpyrazole.

4. A process according to claim 1, wherein seed grains containing the compound of formula (I) are sown on land frequented or capable of being frequented by birds.

5. A process according to claim 4, wherein the compound of formula (I) is 5-amino-3-cyano-1-(2,6-dichloro-4-trifluoromethylphenyl)-4-trifluoromethylsulfinylpyrazole.

6. A process according to claim 1, wherein the crops are protected against birds selected from the group consisting of the Corvidae, the Sturnidae, the passerines, the Galliformes, and the Columbiformes.

7. A process according to claim 3, wherein the crops are protected against birds selected from the group consisting of the Corvidae, the Sturnidae, the passerines, the Galliformes, and the Columbiformes.

8. A process according to claim 4, wherein the crops are protected against birds selected from the group consisting of the Corvidae, the Sturnidae, the passerines, the Galliformes, and the Columbiformes.

9. A process according to claim 5, wherein the crops are protected against birds selected from the group consisting of the Corvidae, the Sturnidae, the passerines, the Galliformes, and the Columbiformes.

10. A process according to claim 6, wherein the birds are crows, starlings, pheasants, partridges, pigeons or turtledoves.

11. A process according to claim 7, wherein the birds are crows, starlings, pheasants, partridges, pigeons or turtledoves.

12. A process according to claim 8, wherein the birds are crows, starlings, pheasants, partridges, pigeons or turtledoves.

13. A process according to claim 9, wherein the birds are crows, starlings, pheasants, partridges, pigeons or turtledoves.

14. A process according to claim 1, wherein the compound of formula (I) is applied in the form of a composition comprising a compound of formula (I) in an amount effective to repel birds and an agronomically acceptable inert solid or liquid vehicle.

15. A process according to claim 14, wherein the compound of formula (I) is 5-amino-3-cyano-1-(2,6-dichloro-4-trifluoromethylphenyl)-4-trifluoromethylsulfinylpyrazole.

16. A process according to claim 14, wherein the composition is applied to cultivated ground after sowing.

17. A process according to claim 15, wherein the composition is applied to cultivated ground after sowing.

18. A process according to claim 14, wherein the composition is applied to cultivated ground before sowing.

19. A process according to claim 15, wherein the composition is applied to cultivated ground before sowing.

20. A process according to claim 14, wherein the composition is applied to the crop seed.

21. A process according to claim 15, wherein the composition is applied to the crop seed.

22. A process according to claim 1, wherein the compound of formula (I) is applied to the crop at a dose of from approximately 0.01 kg/ha to approximately 1 kg/ha.

23. A process according to claim 22, wherein the compound of formula (I) is 5-amino-3-cyano-1-(2,6-dichloro-4-trifluoromethylphenyl)-4-trifluoromethylsulfinylpyrazole.

24. A process according to claim 22, wherein the dose is between 0.02 and 0.3 kg/ha.

25. A process according to claim 24, wherein the compound of formula (I) is 5-amino-3-cyano-1-(2,6-dichloro-4-trifluoromethylphenyl)-4-trifluoromethylsulfinylpyrazole.

26. A process according to claim 1, wherein the compound of formula (I) is applied to the crop seed at a dose of 2 to 1000 g per quintal of seed.

27. A process according to claim 26, wherein the compound of formula (I) is 5-amino-3-cyano-1-(2,6-dichloro-4-trifluoromethylphenyl)-4-trifluoromethylsulfinylpyrazole.

28. A process according to claim 26, wherein the dose is 5 to 800 g per quintal of seed.

29. A process according to claim 28, wherein the compound of formula (I) is 5-amino-3-cyano-1-(2,6-dichloro-4-trifluoromethylphenyl)-4-trifluoromethylsulfinylpyrazole.

* * * * *